(12) United States Patent
Endo et al.

(10) Patent No.: US 10,417,517 B2
(45) Date of Patent: Sep. 17, 2019

(54) MEDICAL IMAGE CORRELATION APPARATUS, METHOD AND STORAGE MEDIUM

(71) Applicant: CANON KABUSHIKI KAISHA, Tokyo (JP)

(72) Inventors: Takaaki Endo, Urayasu (JP); Kiyohide Satoh, Kawasaki (JP)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

(21) Appl. No.: 15/292,462

(22) Filed: Oct. 13, 2016

(65) Prior Publication Data

US 2017/0032533 A1 Feb. 2, 2017

Related U.S. Application Data

(63) Continuation of application No. 13/744,619, filed on Jan. 18, 2013, now abandoned.

(30) Foreign Application Priority Data

Jan. 27, 2012 (JP) .................................. 2012-015934

(51) Int. Cl.
*G06K 9/46* (2006.01)
*A61B 6/00* (2006.01)
(Continued)

(52) U.S. Cl.
CPC .............. *G06K 9/46* (2013.01); *A61B 8/085* (2013.01); *A61B 8/14* (2013.01); *A61B 8/465* (2013.01);
(Continued)

(58) Field of Classification Search
CPC ........... G06T 2207/10081; G06T 2207/10088; G06T 2207/30004; G06T 7/0012;
(Continued)

(56) References Cited

U.S. PATENT DOCUMENTS 6,336,899 B1 * 1/2002 Yamazaki ............ A61B 8/0833
128/916
8,134,554 B1 * 3/2012 Huang .................. G06T 11/008
345/424
(Continued)

FOREIGN PATENT DOCUMENTS

JP 2008-086742 4/2008
JP 2008-100094 5/2008
(Continued)

OTHER PUBLICATIONS

Office Action dated Nov. 16, 2015 in counterpart Japanese patent application 2012-015934, with partial translation.
(Continued)

*Primary Examiner* — Kenny A Cese
(74) *Attorney, Agent, or Firm* — Venable LLP (57) ABSTRACT

An image processing apparatus has a selection unit configured to select at least a first region of interest from regions of interest set in an imaging target, an image obtainment unit configured to obtain a first image representing the imaging target, and a second image from an imaging apparatus that images at least part of the imaging target, an information obtainment unit configured to obtain information of an existence range, and a display control unit configured to add, to the first image, displays representing positions of set regions of interest, and when the second image contains the existence range of the selected region of interest, display the existence range of the selected region of interest on the second image, and when the second image contains the existence range of an unselected region of interest, hide the existence range information.

17 Claims, 7 Drawing Sheets

(51) Int. Cl.
    *A61B 8/08*            (2006.01)
    *A61B 8/14*            (2006.01)
    *A61B 8/00*            (2006.01)
    *G06T 7/30*            (2017.01)
    *G06T 7/11*            (2017.01)

(52) U.S. Cl.
    CPC ................ *G06T 7/11* (2017.01); *G06T 7/30* (2017.01); *A61B 6/466* (2013.01); *A61B 6/469* (2013.01); *A61B 6/5235* (2013.01); *A61B 6/5247* (2013.01); *A61B 8/469* (2013.01); *A61B 8/5246* (2013.01); *A61B 8/5261* (2013.01); *G06T 2207/10072* (2013.01); *G06T 2207/10136* (2013.01); *G06T 2207/20104* (2013.01); *G06T 2207/20221* (2013.01); *G06T 2207/30068* (2013.01)

(58) Field of Classification Search
    CPC .......... G06T 19/00; G06T 2207/10132; G06T 2200/04; G06T 2207/30096; G06T 2207/10116; G06T 2207/20221; G06T 2207/10136; G06T 3/0068; G06T 17/00; G06F 17/30247; A61B 6/466; A61B 6/5235; A61B 6/5247; A61B 6/469; A61B 8/5246; A61B 8/5261
See application file for complete search history.

(56) References Cited

U.S. PATENT DOCUMENTS

| | | | |
|---|---|---|---|
| 8,226,560 B2 | 7/2012 | Arai et al. | |
| 2004/0247174 A1* | 12/2004 | Lyons | G06F 3/04845 |
| | | | 382/154 |
| 2005/0090743 A1* | 4/2005 | Kawashima | A61B 5/06 |
| | | | 600/443 |
| 2005/0206726 A1* | 9/2005 | Yoshida | H04N 7/181 |
| | | | 348/143 |
| 2006/0280347 A1 | 12/2006 | Shirata | 382/128 |
| 2007/0100226 A1* | 5/2007 | Yankelevitz | A61B 5/1075 |
| | | | 600/407 |
| 2007/0167784 A1 | 7/2007 | Shekhar | 600/443 |
| 2009/0129650 A1 | 5/2009 | Hawkes et al. | 382/131 |
| 2009/0202124 A1 | 8/2009 | Matsuda | 382/128 |
| 2009/0285460 A1* | 11/2009 | Ishikawa | G06K 9/48 |
| | | | 382/128 |
| 2009/0310847 A1* | 12/2009 | Matsuzaki | A61B 6/12 |
| | | | 382/132 |
| 2010/0324422 A1 | 12/2010 | Wanda et al. | 600/443 |
| 2011/0158491 A1 | 6/2011 | Markova et al. | 382/128 |
| 2011/0176716 A1* | 7/2011 | Kim | G06T 3/0075 |
| | | | 382/131 |
| 2011/0178389 A1 | 7/2011 | Kumar et al. | 600/411 |
| 2011/0254937 A1 | 10/2011 | Yoshino | 348/65 |
| 2011/0262015 A1 | 10/2011 | Ishikawa et al. | 382/128 |
| 2012/0136882 A1 | 5/2012 | Kawagishi et al. | 707/758 |
| 2012/0169882 A1* | 7/2012 | Millar | G08B 13/19608 |
| | | | 348/159 |
| 2012/0262460 A1 | 10/2012 | Endo et al. | 345/441 |
| 2013/0051646 A1 | 2/2013 | Nakano et al. | 382/131 |
| 2013/0188851 A1 | 7/2013 | Miyasa et al. | 382/131 |
| 2013/0322717 A1* | 12/2013 | Bar-Shalev | G06T 7/0044 |
| | | | 382/131 |
| 2014/0139621 A1* | 5/2014 | Shinozaki | H04N 5/23238 |
| | | | 348/36 |

FOREIGN PATENT DOCUMENTS

| | | |
|---|---|---|
| JP | 2008-246264 | 10/2008 |
| JP | 2008-279272 | 11/2008 |
| JP | 2010-051817 | 3/2010 |
| JP | 2010-194007 | 9/2010 |
| WO | WO 2011/074162 | 6/2011 |

OTHER PUBLICATIONS

Extended European Search Report dated May 17, 2013 in counterpart European Patent Application No. 13152765.7.

\* cited by examiner

MEDICAL IMAGE CORRELATION APPARATUS, METHOD AND STORAGE MEDIUM

RELATED APPLICATIONS

This application is a continuation of application Ser. No. 13/744,619, filed Jan. 18, 2013, claims the benefit of that application under 35 U.S.C. § 120, and claims the benefit under 35 U.S.C. § 119 of Japanese Patent Application No. 2012-015934, filed on Jan. 27, 2012. The entire contents of both of those earlier applications are hereby incorporated by reference herein.

BACKGROUND OF THE INVENTION

Field of the Invention

The present invention relates to a technique of performing navigation display for searching for the position of a lesion using an image obtained by an imaging apparatus such as an ultrasonic imaging apparatus.

Description of the Related Art

In the medical field, a doctor displays, on the monitor, a medical image obtained by capturing a target object, interprets the displayed medical image, and diagnoses the lesion site.

Medical image collecting apparatuses (to be referred to as modalities hereinafter) for capturing a medical image include an ultrasonic image diagnostic apparatus, a resonant magnetic coupling imaging apparatus (to be referred to as an MRI apparatus hereinafter), and an X-ray computed tomography apparatus (to be referred to as an X-ray CT apparatus hereinafter). It is difficult to accurately diagnose the state of a lesion site by only observing a medical image captured by an individual modality. Hence, an attempt has been made to accurately diagnose the state of a lesion site by comparing lesion sites in medical images captured by a plurality of modalities or medical images captured on or at different dates and times.

In diagnosis based on a plurality of medical images, for example, while looking at the image of a lesion site (to be referred to as a lesion site of interest hereinafter) indicated in one medical image (to be referred to as a reference image hereinafter), the operator searches another medical image (to be referred to as a target image hereinafter) for a lesion site (to be referred to as a corresponding lesion site hereinafter) corresponding to the lesion site of interest, and specifies it.

Japanese Patent Laid-Open No. 2008-279272 discloses a method in which a square having a size and color based on the distance and direction of an image track point (lesion site of interest), which is selected from a past ultrasonic tomogram, from a current ultrasonic tomogram is superimposed and displayed as an in-plane indicator on the current ultrasonic tomogram. Japanese Patent Laid-Open No. 2008-279272 further discloses a technique of selecting whether to hide or remove all or some in-plane indicators from the display.

In some cases, an alignment error is generated due to the difference in imaging posture between different medical images, or a position-specifying error is generated for a region of interest such as a lesion site. It is conceivable to present an "existence region" where a region of interest may exist.

In addition, when a plurality of regions of interest exist, the relationship between them should be grasped. However, if a plurality of existence regions are displayed on an ultrasonic tomogram, it is hard for the observer to recognize an existence region where the current region of interest exists. This may affect efficient diagnosis.

SUMMARY OF THE INVENTION

The present invention has been made to solve the above problems, and provides a technique capable of presenting a display for allowing easy search of a target image for a region of interest selected from regions of interest such as a plurality of lesion sites.

According to one aspect of the present invention, there is provided an image processing apparatus comprising: a selection unit configured to select at least a first region of interest from a plurality of regions of interest set in an imaging target; an image obtainment unit configured to obtain a first image representing the imaging target, and a second image from an imaging apparatus that images at least part of the imaging target; an information obtainment unit configured to obtain information of an existence range representing a range where a region of interest may exist on the second image; and a display control unit configured to add, to the first image, displays representing positions of the plurality of set regions of interest, and when the second image contains the existence range of the selected region of interest, display the existence range of the selected region of interest on the second image, and when the second image contains the existence range of an unselected region of interest, hide the existence range information.

Further features of the present invention will become apparent from the following description of exemplary embodiments with reference to the attached drawings.

DESCRIPTION OF THE EMBODIMENTS

Embodiments of an image processing apparatus according to the present invention will now be described with reference to the accompanying drawings. However, the scope of the invention is not limited to illustrated examples.

(First Embodiment)

When one of a plurality of regions of interest in three-dimensional image data is selected as one region of interest, an ultrasonic imaging system according to the embodiment changes the display mode to non-display of information representing the three-dimensional position of a region of no interest on the current ultrasonic tomogram. Also, the ultrasonic imaging system changes the display mode of a figure representing the existence region of a corresponding region on the ultrasonic tomogram that corresponds to the unselected region of no interest, so that the region of no interest becomes less conspicuous than the region of interest (for example, the color is changed into a light one). This enables the operator to easily search for and identify a corresponding region on the ultrasonic tomogram (as a medical image).

The region of interest is, for example, a lesion site. The region of interest is, for example, a lesion site to be diagnosed among a plurality of lesion sites. However, the region of interest is not limited to a lesion site, and suffices to be a region worth noting for a person who makes a diagnosis. As the information representing a three-dimensional position, the distance and direction are displayed in addition to a coordinate value.

The embodiment will exemplify a case in which the breast of a human body serves as a target object. An ultrasonic imaging system according to the embodiment will be explained.

The ultrasonic imaging system includes an image processing apparatus 100, an ultrasonic image diagnostic apparatus 180 capable of ultrasonic imaging using an ultrasonic probe, and a display unit 160. The ultrasonic imaging system is connected to a data server 190 which stores images from a three-dimensional image collecting apparatus 170.

Figure 1:
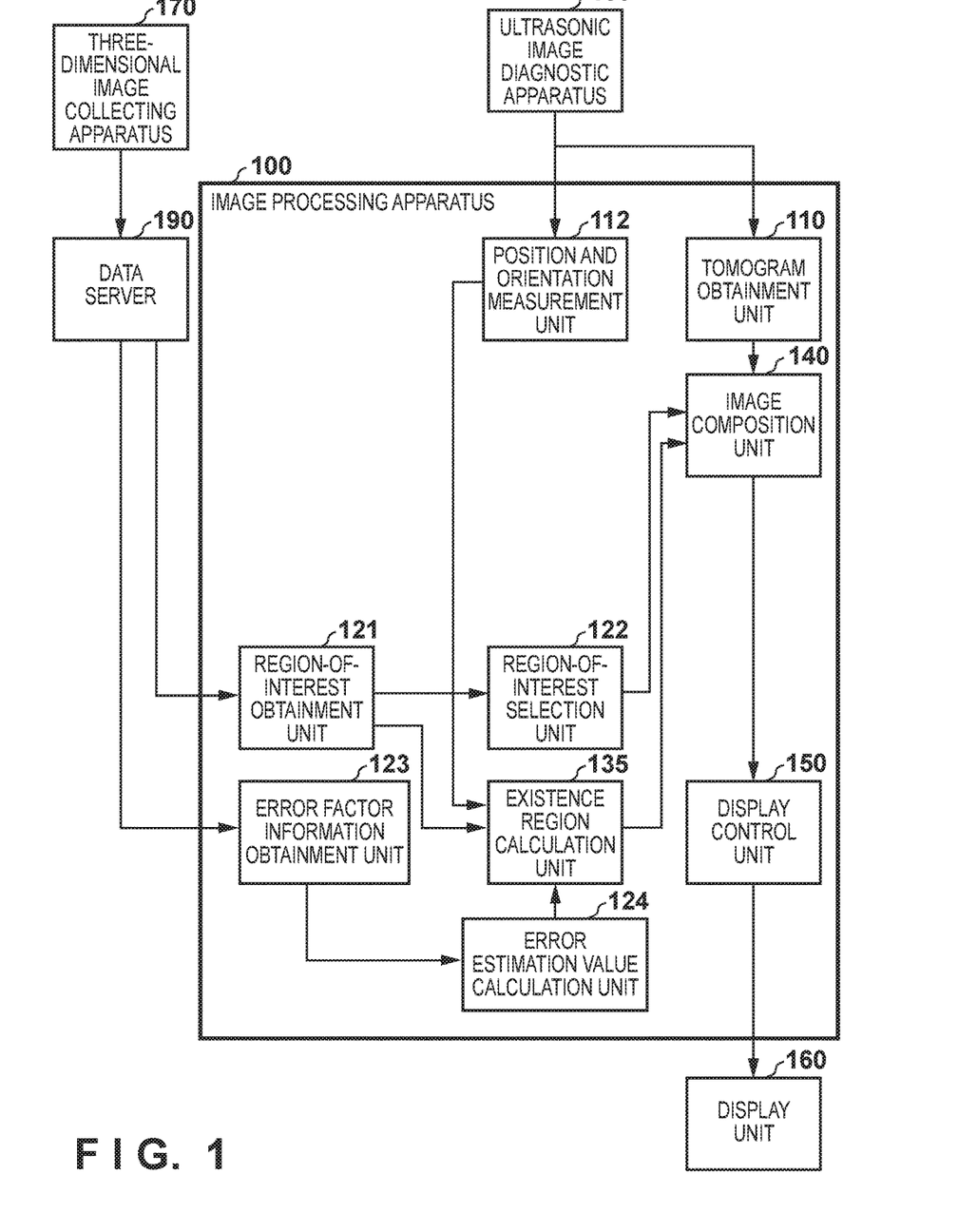
FIG. 1 is a block diagram showing the device arrangement of an image processing apparatus according to the first embodiment.

FIG. 1 shows the arrangement of the ultrasonic imaging system according to the embodiment. As shown in FIG. 1, the image processing apparatus 100 in the embodiment performs navigation display for imaging a subject during ultrasonic imaging by an ultrasonic imaging apparatus, and the same apparatus performs the searching for the position of a lesion. The image processing apparatus 100 includes a tomogram obtainment unit 110, position and orientation measurement unit 112, region-of-interest obtainment unit 121, region-of-interest selection unit 122, error factor information obtainment unit 123, error estimation value calculation unit 124, existence region calculation unit 135, image composition unit 140, and display control unit 150. The image processing apparatus 100 is connected to the data server 190, and the ultrasonic image diagnostic apparatus 180 which captures the ultrasonic tomogram of a breast.

[Obtainment of Region of Interest]

The data server 190 holds information representing a plurality of lesion sites in three-dimensional image data. The three-dimensional image data is an image obtained by capturing a subject in advance by an MRI apparatus, X-ray CT apparatus, or the like serving as the three-dimensional image collecting apparatus 170. A case in which an MRI apparatus is used as the three-dimensional image collecting apparatus 170 will be exemplified. Information representing a lesion site is, for example, the position of the lesion site (barycentric position of the region), or the coordinates of a point group positioned at the boundary of the region of a lesion site of interest. In the following description, information representing a lesion site is the position of a lesion site, and the position of the lesion site is expressed in the MRI apparatus coordinate system. The position of a lesion site held in the data server 190 is obtained by the region-of-interest obtainment unit 121 and input to the image processing apparatus 100.

[Obtainment of Error Factor Information]

In addition to this information, the data server 190 holds error factor information (details of which will be described later) for calculating the error estimation value of a corresponding lesion site. In other words, the error factor information is information for calculating the existence region of a corresponding lesion site on an ultrasonic tomogram. The error factor information held in the data server 190 is input to the image processing apparatus 100 via the error factor information obtainment unit 123.

[Obtainment of Tomogram]

The ultrasonic image diagnostic apparatus 180 captures ultrasonic tomograms of a subject in real time. Ultrasonic tomograms are sequentially obtained by the tomogram obtainment unit 110 and sequentially input to the image processing apparatus 100. The position and orientation of the ultrasonic probe are measured by a position and orientation sensor (not shown), measured by the position and orientation measurement unit 112, and input to the image processing apparatus 100. The position and orientation of the ultrasonic probe are expressed by, for example, a position and orientation in a reference coordinate system using a subject as a reference. The position and orientation measurement unit 112 measures the position and orientation of the ultrasonic probe in the reference coordinate system, and based on them, calculates the position and orientation of an ultrasonic tomogram in the MRI apparatus coordinate system.

[Calculation of Error Estimation Value]

The error estimation value calculation unit 124 calculates the error estimation value of a corresponding lesion site based on error factor information obtained by the error factor information obtainment unit 123. The error estimation value calculation unit 124 outputs the calculated error estimation value to the existence region calculation unit 135.

[Determining of Existence Region]

Based on the position of a lesion site that is obtained by the region-of-interest obtainment unit 121, and the position and orientation of an ultrasonic tomogram that are measured by the position and orientation measurement unit 112, the existence region calculation unit 135 estimates the position of a corresponding lesion site in an ultrasonic coordinate system that corresponds to each lesion site in three-dimensional image data. The ultrasonic coordinate system is a three-dimensional coordinate system using an ultrasonic tomogram as a reference. The ultrasonic coordinate system can be defined as, for example, a coordinate system in which one point on the tomogram is set as the origin, the x- and y-axes are set on the plane of the tomogram, and the z-axis is set in a direction perpendicular to the plane. Based on the estimated corresponding lesion site, and an error estimation value estimated by the error estimation value calculation unit 124, the existence region calculation unit 135 specifies the position of each corresponding lesion site by calculating a region (existence region) where the corresponding lesion site may exist on the ultrasonic tomogram.

[Selection of Lesion Site of Interest]

Based on an instruction from the operator, the region-of-interest selection unit 122 selects a lesion site of interest from lesion sites obtained by the region-of-interest obtainment unit 121. Note that lesion sites other than the selected lesion site of interest serve as "lesion sites of no interest".

[Composition of Images]

The image composition unit 140 obtains, from the existence region calculation unit 135, information representing the existence region of each corresponding lesion site, and superimposes and renders, on an ultrasonic tomogram obtained from the tomogram obtainment unit 110, a figure representing the existence region of each corresponding lesion site. If the existence region of a lesion site of interest does not exist on a slice, the image composition unit 140 calculates the three-dimensional position (distance and direction) of the lesion site of interest on the ultrasonic tomogram, and superimposes and renders, on the ultrasonic tomogram, information representing the calculated distance and direction.

[Display Control]

The display control unit 150 controls the display unit 160 to cause it to display an image obtained by the image composition unit 140. More specifically, the display control unit 150 controls the display unit 160 to cause it to display the positions of a plurality of regions of interest obtained by the region-of-interest obtainment unit 121, and display the existence region of a region of interest obtained by the existence region calculation unit 135 on an ultrasonic tomogram. By displaying the image obtained by the image composition unit 140, the display control unit 150 changes, by different methods in accordance with a selection, the display mode of the positions of regions of interest other than a selected region of interest, and that of existence regions corresponding to the regions of interest other than the selected region of interest.

Note that at least some of the respective units shown in FIG. 1 may be implemented as independent apparatuses. Alternatively, they may be implemented as software programs which are installed in one or a plurality of computers and executed by the CPUs of the computers to implement the functions. In the embodiment, the various units are implemented by software programs which are installed in a single computer.

[Basic Arrangement of Computer]

Figure 2:
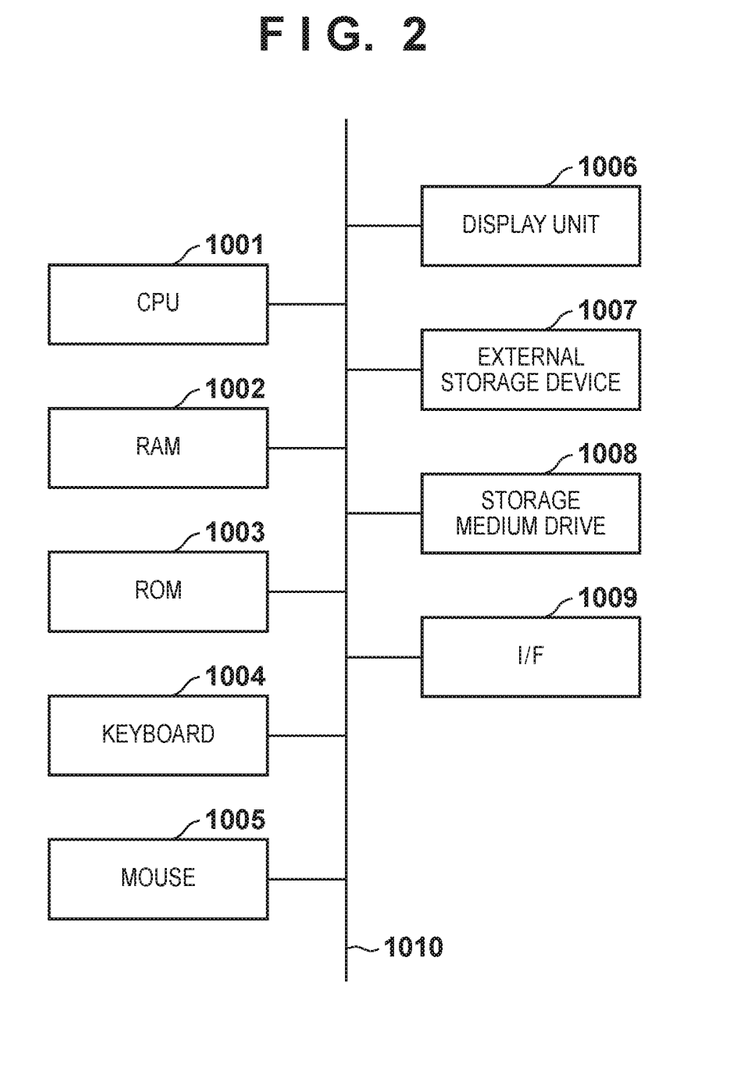
FIG. 2 is a block diagram showing the basic arrangement of a computer which can implement each unit of the image processing apparatus by software according to the first embodiment.

FIG. 2 is a block diagram showing the basic arrangement of a computer which executes software programs to implement the functions of the various units (to be described later). These units are the tomogram obtainment unit 110, position and orientation measurement unit 112, region-of-interest obtainment unit 121, region-of-interest selection unit 122, error factor information obtainment unit 123, error estimation value calculation unit 124, existence region calculation unit 135, image composition unit 140, and display control unit 150.

A CPU 1001 controls the overall computer using programs and data which are stored in a RAM 1002 and ROM 1003. The CPU 1001 controls execution of programs corresponding to the tomogram obtainment unit 110, position and orientation measurement unit 112, region-of-interest obtainment unit 121, region-of-interest selection unit 122, error factor information obtainment unit 123, error estimation value calculation unit 124, existence region calculation unit 135, image composition unit 140, and display control unit 150.

The RAM 1002 has an area for temporarily storing programs and data loaded from an external storage device 1007 and storage medium drive 1008. In addition, the RAM 1002 has a work area necessary to perform various processes by the CPU 1001.

The ROM 1003 generally stores computer programs, setting data, and the like. A keyboard 1004 and mouse 1005 are input devices, and the operator can use them to input various instructions to the CPU 1001.

A display unit 1006 is formed from a CRT, liquid crystal display, or the like, and corresponds to the display unit 160. The display unit 1006 can display a composite image generated by the image composition unit 140, a message and GUI to be displayed for image processing, and the like.

The external storage device 1007 is a device functioning as a large-capacity information storage device such as a hard disk drive. An OS (Operating System), programs to be executed by the CPU 1001, and the like are saved in the external storage device 1007. In the description of the embodiment, information to be stored for subsequent use is saved in the external storage device 1007, and loaded into the RAM 1002, as needed.

The storage medium drive 1008 reads out programs and data stored in a storage medium such as a CD-ROM or DVD-RAM in accordance with an instruction from the CPU 1001, and outputs them to the RAM 1002 or external storage device 1007.

An I/F 1009 is formed from an analog video port, a digital I/O port such as an IEEE1394 port, an Ethernet® port for outputting outside information such as a composite image, and the like. Data input from the respective ports are loaded into the RAM 1002 via the I/F 1009. The I/F 1009 implements some of the functions of the tomogram obtainment unit 110, position and orientation measurement unit 112, region-of-interest obtainment unit 121, and error factor information obtainment unit 123. These building components are connected to each other by a bus 1010.

Figure 3:
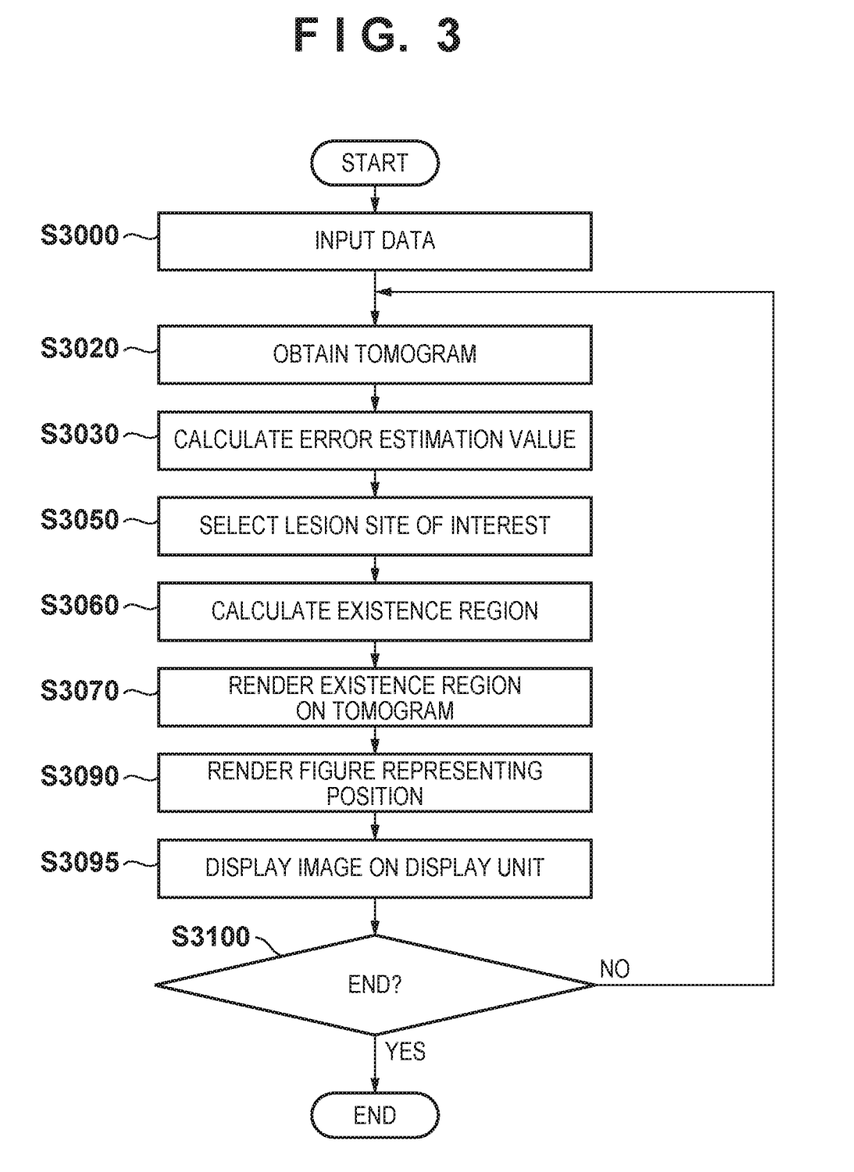
FIG. 3 is a flowchart showing a processing sequence by the image processing apparatus according to the first embodiment.

FIG. 3 is a flowchart showing an overall processing sequence to be performed by the image processing apparatus 100. In the embodiment, this flowchart is implemented when the CPU 1001 executes a program for implementing the function of each unit. It is assumed that program codes complying with this flowchart have already been loaded from, for example, the external storage device 1007 into the RAM 1002 before performing the following processing.

[Step S3000: Input of Data]

In step S3000, in the role of the region-of-interest obtainment unit 121, the image processing apparatus 100 obtains the position of a lesion site as the position of a region of interest from the data server 190. In the role of the error factor information obtainment unit 123, the image processing apparatus 100 obtains, from the data server 190, various kinds of error factor information used to calculate an error estimation value. For example, information representing the type of position and orientation sensor (for example, sensor A or sensor B) which measures the position and orientation of the ultrasonic probe is obtained as error factor information.

[Step S3020: Obtainment of Tomogram]

In step S3020, in the role of the tomogram obtainment unit 110, the image processing apparatus 100 obtains an ultrasonic tomogram from the ultrasonic image diagnostic apparatus 180. In the role of the position and orientation measurement unit 112, the image processing apparatus 100 obtains, from the ultrasonic image diagnostic apparatus 180, the position and orientation of the ultrasonic probe obtained when the ultrasonic tomogram was captured. By using calibration data stored in advance as a known value, the image processing apparatus 100 calculates the position and orientation of the ultrasonic tomogram in the MRI apparatus coordinate system from the position and orientation of the ultrasonic probe in the reference coordinate system.

[Step S3030: Calculation of Error Estimation Value]

In step S3030, in the role of the error estimation value calculation unit 124, the image processing apparatus 100 calculates an error estimation value based on various kinds of error factor information obtained in step S3000. The processing of calculating an error estimation value can be executed based on, for example, the characteristics of the position and orientation sensor which measures the position and orientation of the ultrasonic probe. The reference value of an error is set in advance for each type of position and orientation sensor so that a value can be selected in accordance with the type of sensor used. For example, when the error factor information input in step S3000 is information representing that sensor A serving as an optical sensor is used, an error estimation value can be calculated as a value smaller than that when sensor B serving as a magnetic sensor is used.

Note that the error estimation processing may be another processing. For example, an error may arise from an alignment algorithm for a three-dimensional MRI image or a three-dimensional CT image obtained by the three-dimensional image collecting apparatus 170, and an ultrasonic tomogram obtained by the ultrasonic image diagnostic apparatus 180. In particular, when an MRI image captured at the prone position and an ultrasonic image captured at the supine position are aligned while being deformed, an error may arise from the deformation algorithm. Even for such an error arising from the deformation, an empirically obtained error magnitude is stored in advance in the memory and used for estimation of the magnitude of an error.

[Step S3050: Selection of Lesion Site of Interest]

In step S3050, in the role of the region-of-interest selection unit 122, the image processing apparatus 100 selects, based on an instruction from the operator, at least one lesion site of interest from lesion sites obtained by the region-of-interest obtainment unit 121. For example, respective lesion sites are numbered in advance so that the image processing apparatus 100 can obtain an instruction input by the operator by, for example, pressing a numeric key of the keyboard 1004 that corresponds to the number of a lesion site of interest.

[Step S3060: Calculation of Existence Region]

In step S3060, in the role of the existence region calculation unit 135, the image processing apparatus 100 calculates the existence region of a corresponding lesion site corresponding to each of the lesion sites on the ultrasonic tomogram obtained in step S3020.

More specifically, first, the existence region calculation unit 135 estimates the position of a corresponding lesion site in the ultrasonic coordinate system that corresponds to the position of each lesion site obtained by the region-of-interest obtainment unit 121. This estimation can be performed based on the position and orientation of the ultrasonic tomogram that have been measured by the position and orientation measurement unit 112.

Then, the existence region calculation unit 135 calculates the existence region of each corresponding lesion site on the ultrasonic tomogram based on the estimated position of each corresponding lesion site, and the error estimation value calculated in step S3030. The three-dimensional existence region of the corresponding lesion site in the ultrasonic coordinate system is defined as a sphere having the estimated position of the corresponding lesion site as the center and the error estimation value as the radius. The existence region of the corresponding lesion site on the ultrasonic tomogram is defined as a circle which is a region (slice of the sphere) where the sphere and the tomogram cross each other.

As the existence region of each corresponding lesion site, the existence region calculation unit 135 calculates the center position and radius of the circle on the ultrasonic tomogram. Note that the method of calculating the cross region of a sphere and plane that are defined in a three-dimensional space is well known, and a description thereof will be omitted. If the sphere regarding the lesion site of interest selected by the region-of-interest selection unit 122, and the tomogram do not cross each other, information "the existence region of the lesion site of interest does not exist on the slice" is saved.

[Step S3070: Rendering Existence Region on Tomogram]

Figure 4:
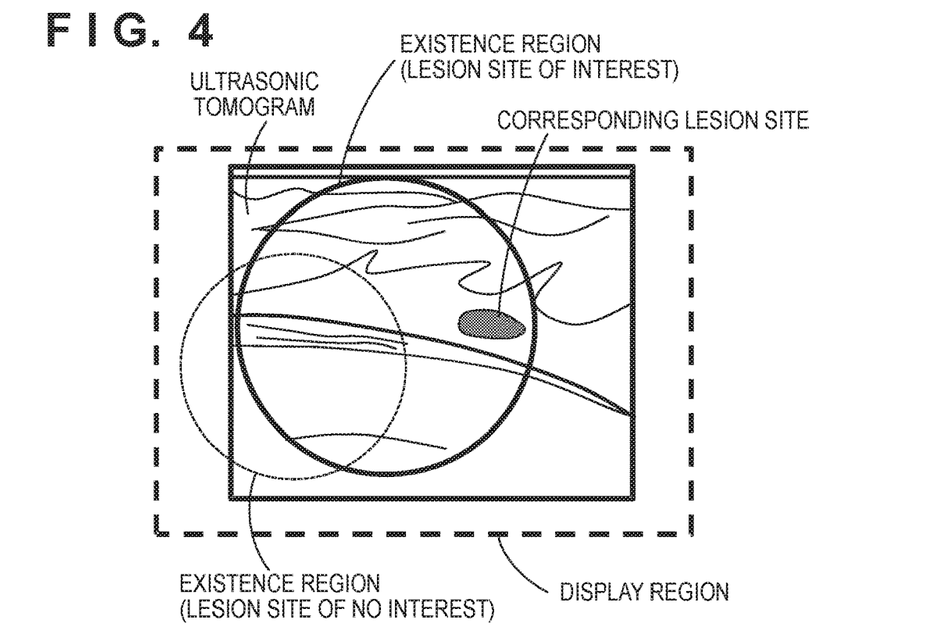
FIG. 4 is a view for explaining a display method by the image processing apparatus according to the first embodiment.

In step S3070, as processing of the image composition unit 140, the image processing apparatus 100 generates an image in which a figure representing the existence region of each corresponding lesion site that has been calculated in step S3060 is superimposed and rendered on the ultrasonic tomogram. For example, the range where the corresponding lesion site may exist is rendered by a line of a closed curve. At this time, a figure representing the existence region of a lesion site of no interest which is positioned in a different position from the lesion site of interest selected by the region-of-interest selection unit 122 is rendered in a display mode in which the figure becomes less conspicuous than a figure representing the existence region of the lesion site of interest. For example, the color of the figure representing the existence region is changed into a lighter color. FIG. 4 exemplifies an image generated by the processing of this step. If no lesion site of interest has been selected in step S3050, figures representing the existence regions of respective lesion sites are rendered in the same display mode without discrimination.

If it is determined in step S3060 that "the existence region of the lesion site of interest does not exist on the slice", the processing of this step may not be executed. In this case, the existence region of a lesion site of no interest, which means a site containing a lesion but that is not of current interest, is rendered only when the existence region of the lesion site of interest exists on the slice.

[Step S3090: Rendering Figure Representing Position]

Figure 5:
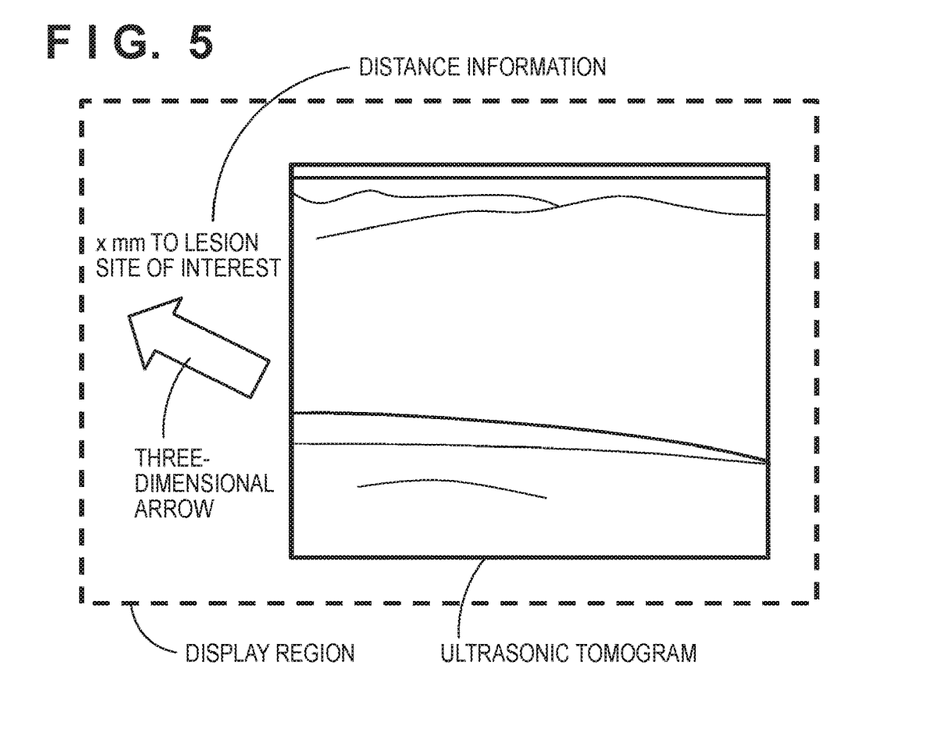
FIG. 5 is a view for explaining the display method by the image processing apparatus according to the first embodiment.

In step S3090, in the role of the image composition unit 140, if it is determined that "the existence region of the lesion site of interest does not exist on the slice", the image processing apparatus 100 renders a figure representing the position of the lesion site of interest. More specifically, the three-dimensional position (distance and direction) of the lesion site of interest on the ultrasonic tomogram is calculated. Then, an image is generated in which information representing the calculated distance and direction is superimposed on the image processed in step S3070. FIG. 5 exemplifies an image generated by the processing of this step. If no lesion site of interest has been selected in step S3050, figures representing the positions of respective lesion sites are rendered in the same display mode without discrimination. The example in FIG. 5 shows the ultrasonic tomogram with no lesion (no region of interest) and a three-dimensional arrow with a label giving distance information to the lesion site of interest, such as "xmm to lesion site of interest".

[Step S3095: Display of Image]

In step S3095, in the role of the display control unit 150, the image processing apparatus 100 displays the image composited in step S3090 on the display unit 160. If necessary, the image processing apparatus 100 outputs the composite image to the outside via the I/F 1009. Further, the image processing apparatus 100 stores the image in the RAM 1002 so that it can be used from another application.

[Step S3100: Determination of Whether to End Overall Processing]

In step S3100, the image processing apparatus 100 determines whether to end the overall processing. For example, the image processing apparatus 100 obtains an end instruction based on, for example, pressing of a predetermined key (end key) of the keyboard 1004 by the operator. If the image processing apparatus 100 determines that it is to end the overall processing, it ends the overall processing of the image processing apparatus 100. If the image processing apparatus 100 determines that it is not to end the overall processing, it returns the process to step S3020, and executes again the processes in step S3020 and subsequent steps for a newly captured ultrasonic tomogram. In this manner, the processing of the image processing apparatus 100 is executed.

As described above, the image processing apparatus according to the first embodiment can change, to non-display, the display mode of information representing the three-dimensional position (distance and direction) of a lesion site of no interest on an ultrasonic tomogram. Also, the image processing apparatus can change the display mode of a figure representing the existence region of a lesion site of no interest on the ultrasonic tomogram so that the lesion site of no interest becomes less conspicuous than a lesion site of interest. Since information representing the three-dimensional position (distance and direction) of the lesion site of no interest on the ultrasonic tomogram is not displayed, it does not hinder search for a corresponding lesion site corresponding to the lesion site of interest.

By observing both figures representing the existence regions of a lesion site of interest and a lesion site of no interest, the operator can grasp whether a lesion site which may cause an identification error exists near the lesion site of interest. That is, the image processing apparatus according to the first embodiment can efficiently search a target image for a corresponding lesion site corresponding to a lesion site of interest selected from a plurality of lesion sites in a reference image, and identify the lesion site of interest.

(Modification 1 to First Embodiment)

The above-described embodiment has exemplified a case in which a lesion site of interest is selected based on an instruction from the operator. Alternatively, a lesion site of interest may be selected in advance and held in the data server 190. In this case, the region-of-interest selection unit 122 in FIG. 1 may be omitted, and the region-of-interest selection processing in step S3050 need not be performed.

(Modification 2 to First Embodiment)

The above-described embodiment has exemplified a case in which the color of a figure representing the existence region of a lesion site of no interest is changed into a light color. However, the display mode change method is not limited to this. For example, the thickness or type of the line of the figure may be changed, or the saturation of the color of the figure may be decreased.

(Second Embodiment)

An ultrasonic imaging system according to the second embodiment changes, to non-display, the display mode of a figure representing a region (existence region) where a corresponding lesion site on an ultrasonic tomogram that corresponds to a lesion site (lesion site of no interest) other than a lesion site of interest may exist. Also, the ultrasonic imaging system changes the display mode of a figure representing the position of a lesion site of no interest on a body mark image representing a target object, so that the lesion site of no interest becomes less conspicuous than the lesion site of interest (for example, the color is changed into a light one). This enables the operator to easily search for and identify a corresponding lesion site on the ultrasonic tomogram. A difference of the ultrasonic imaging system according to the second embodiment from the first embodiment will be mainly explained.

Figure 6:
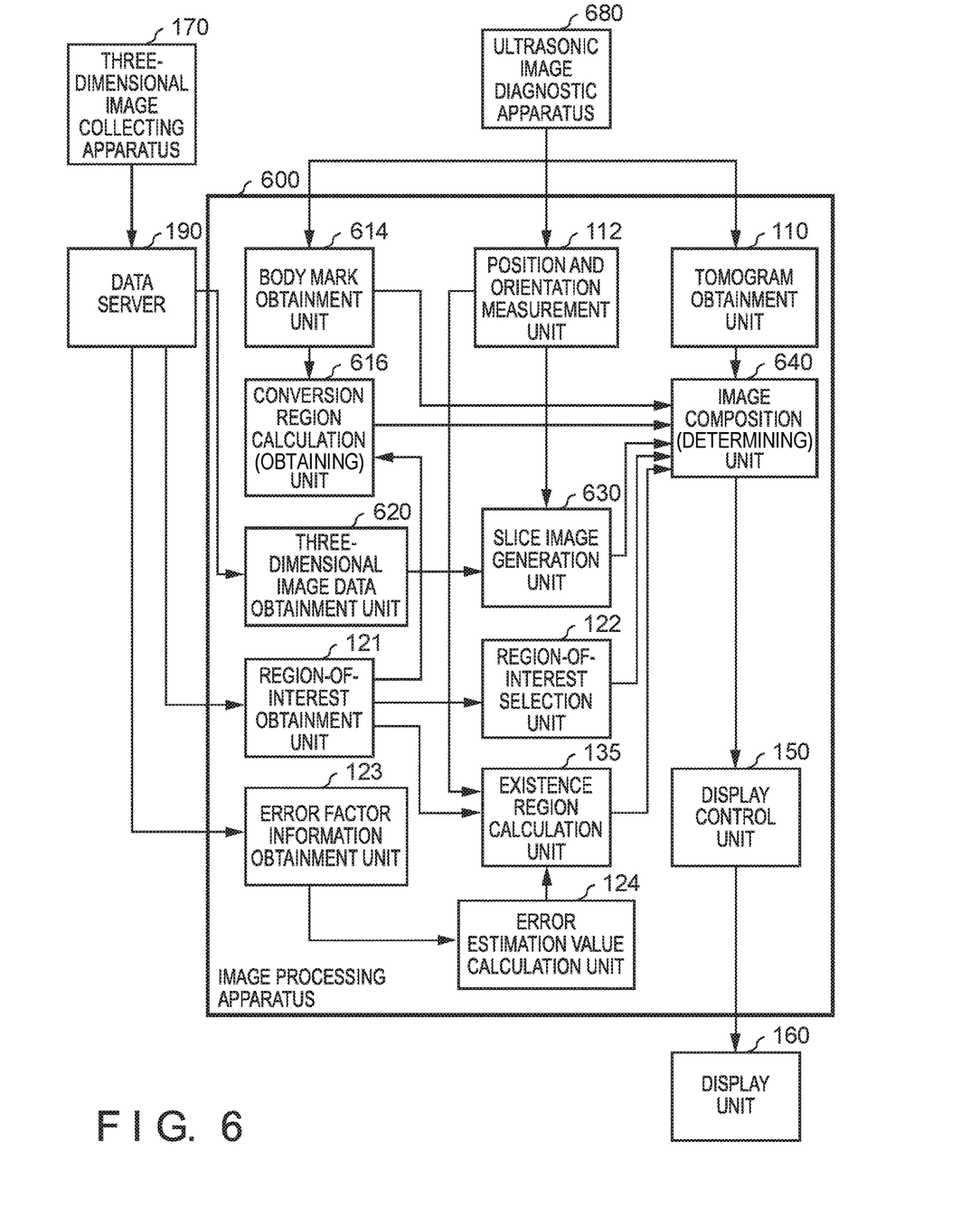
FIG. 6 is a block diagram showing the device arrangement of an image processing apparatus according to the second embodiment.

FIG. 6 shows the arrangement of the ultrasonic imaging system according to the second embodiment. Note that the same reference numerals and symbols as those in FIG. 1 denote the same parts, and a description thereof will not be repeated.

[Obtainment of Three-dimensional Image Data]

Three-dimensional image data held in a data server 190 is obtained by a three-dimensional image data obtainment unit 620 and input to an image processing apparatus 600. In the embodiment, three-dimensional image data is expressed as three-dimensional volume data in which a luminance value is stored in a three-dimensional voxel. Also, the coordinates of each voxel are expressed in the MRI apparatus coordinate system.

[Obtainment of Body Mark]

An ultrasonic image diagnostic apparatus 680 holds a body mark image. This body mark is an image representing the schematic shape of a breast, and is an image for schematically showing the position of a lesion. A body mark for the left breast and a body mark for the right breast which are held in the ultrasonic image diagnostic apparatus 680 are obtained by a body mark obtainment unit 614 and input to the image processing apparatus 600. A conversion region calculation unit 616 converts the position of each lesion site obtained by a region-of-interest obtainment unit 121 into a position in a body mark coordinate system. The body mark coordinate system is a system in which a plane containing the body mark for the left breast and that for the right breast is defined as the x-y plane, and an axis perpendicular to the x-y plane is defined as the z-axis.

[Composition of Images]

A slice image generation unit 630 receives three-dimensional volume data output from the three-dimensional image data obtainment unit 620, and the position and orientation of an ultrasonic tomogram output from a position and orientation measurement unit 112. Based on these data, the slice image generation unit 630 generates a slice image corresponding to the ultrasonic tomogram from the three-dimensional volume data, and outputs it to an image composition unit 640. The image composition unit 640 obtains, from an existence region calculation unit 135, information representing the existence region of a corresponding lesion site. Then, the image composition unit 640 superimposes and renders, on an ultrasonic tomogram obtained from a tomogram obtainment unit 110, information representing the existence region of a corresponding lesion site corresponding to a lesion site of interest selected by a region-of-interest selection unit 122. The image composition unit 640 obtains the position of each lesion site from the conversion region calculation unit 616, and renders a figure representing the position of each lesion site on a body mark obtained from the body mark obtainment unit. Further, the image composition unit 640 generates a composite image by compositing these images and the slice image obtained from the slice image generation unit 630. The image composition unit 640 outputs the composite image to a display control unit 150 or to outside. The display control unit 150 obtains the composite image output from the image composition unit 640, and displays it on a display unit 160.

Figure 7:
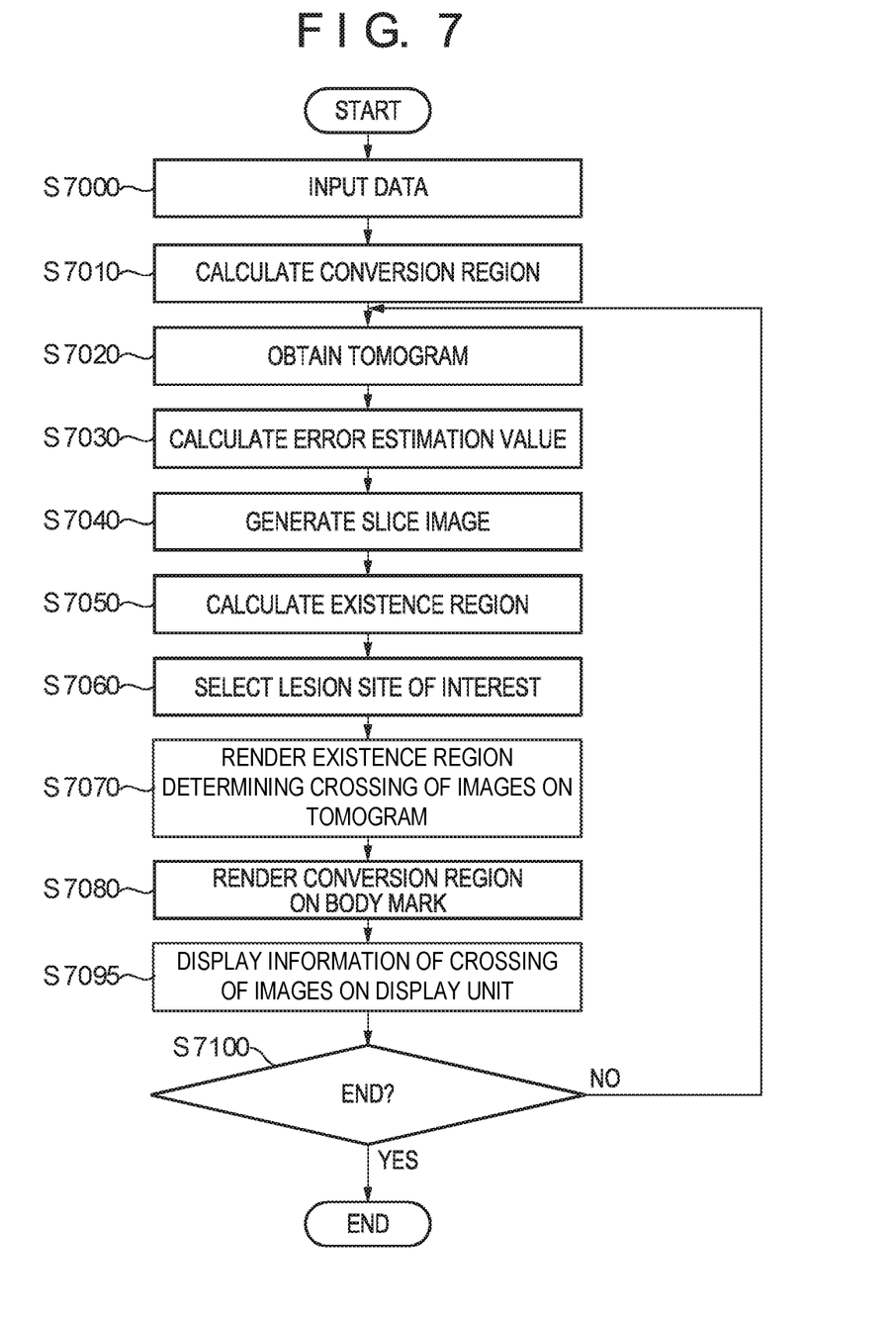
FIG. 7 is a flowchart showing a processing sequence by the image processing apparatus according to the second embodiment.

FIG. 7 is a flowchart showing an overall processing sequence to be performed by the image processing apparatus 600. In the embodiment, this flowchart is implemented when a CPU 1001 executes a program for implementing the function of each unit. Assume that program codes complying with this flowchart have already been loaded from, for example, an external storage device 1007 into a RAM 1002 before performing the following processing.

[Step S7000: Input of Data]

In step S7000, in the role of the three-dimensional image data obtainment unit 620, the image processing apparatus 600 obtains three-dimensional image data from the data server 190, in addition to the processing in step S3000. In the role of the body mark obtainment unit 614, the image processing apparatus 600 obtains a body mark for the left breast and a body mark for the right breast from the ultrasonic image diagnostic apparatus 680.

[Step S7010: Calculation of Conversion Region]

In step S7010, in the role of the conversion region calculation unit 616, the image processing apparatus 600 converts the position of each lesion site obtained by the region-of-interest obtainment unit 121 into a position in the body mark coordinate system. This conversion is disclosed in, for example, Japanese Patent Laid-Open No. 2008-086742. More specifically, coordinate conversion from a position on a breast into a position on a standard body mark representing a breast is executed.

Processes in steps S7020 and S7030 are the same as those in steps S3020 and S3030 in the first embodiment, and a description thereof will be omitted.

[Step S7040: Generation of Slice Image]

In step S7040, in the role of the slice image generation unit 630, the image processing apparatus 600 generates the slice image of a reference image corresponding to an ultrasonic tomogram obtained in step S7020. More specifically, based on the position and orientation of the ultrasonic tomogram obtained in step S7020, the image processing apparatus 600 generates a slice image by extracting the same slice as the ultrasonic tomogram from the three-dimensional volume data obtained in step S7000.

[Step S7050: Selection of Lesion Site of Interest]

In step S7050, in the role of the region-of-interest selection unit 122, the image processing apparatus 600 selects, based on an instruction from the operator, a lesion site of interest from lesion sites obtained by the region-of-interest obtainment unit 121. For example, by clicking a mouse 1005, the operator can select a figure representing the position of a lesion site of interest on the body mark.

Processing in step S7060 is the same as that in step S3060 in the first embodiment, and a description thereof will not be repeated.

[Step S7070: Rendering Existence Region on Tomogram]

In step S7070, the image composition unit 640 of the image processing apparatus 600 generates an image in which a figure representing the existence region of a corresponding lesion site corresponding to the lesion site of interest selected in step S7050 is superimposed and rendered on the ultrasonic tomogram. For example, the range where the corresponding lesion site may exist is rendered by a closed curve. If no lesion site of interest has been selected in step S7050, figures representing the existence regions of respective lesion sites are rendered in the same display mode without discrimination.

[Step S7080: Rendering Conversion Region on Body Mark]

In step S7080, in the role of the image composition unit 640, first, the image processing apparatus 600 selects either the body mark for the left breast or that for the right breast to be used. For example, when a lesion site of interest has been selected in step S7050, it is determined which of the left and right breasts contains the selected lesion site of interest, and then a body mark for use can be selected. More specifically, the distances between the position of the lesion site of interest in the body mark coordinate system that has been calculated in step S7010, and the positions of the left and right nipples in the body mark coordinate system are calculated, and a body mark having a shorter distance can be selected. Alternatively, at which of the positions of the left and right breasts the ultrasonic probe exists is determined based on the position and orientation of the ultrasonic tomogram measured by the position and orientation measurement unit 112, and a body mark for use can be selected.

Then, a figure representing the position of a lesion site is rendered at the position of each lesion site on the selected body mark. At this time, a FIG. representing the position of a lesion site of no interest other than the lesion site of interest selected by the region-of-interest selection unit 122 is rendered in a display mode in which the figure becomes less conspicuous than a figure representing the position of the lesion site of interest. For example, the color of the figure is changed into a light color. If no lesion site of interest has been selected in step S7050, figures representing the positions of respective lesion sites are rendered in the same display mode without discrimination.

Further, the position of the probe in the body mark coordinate system is calculated based on the position and orientation of the ultrasonic tomogram measured by the position and orientation measurement unit 112, and a figure (probe mark) representing the position of the probe is rendered on the body mark.

[Step S7095: Display of Image]

Figure 8:
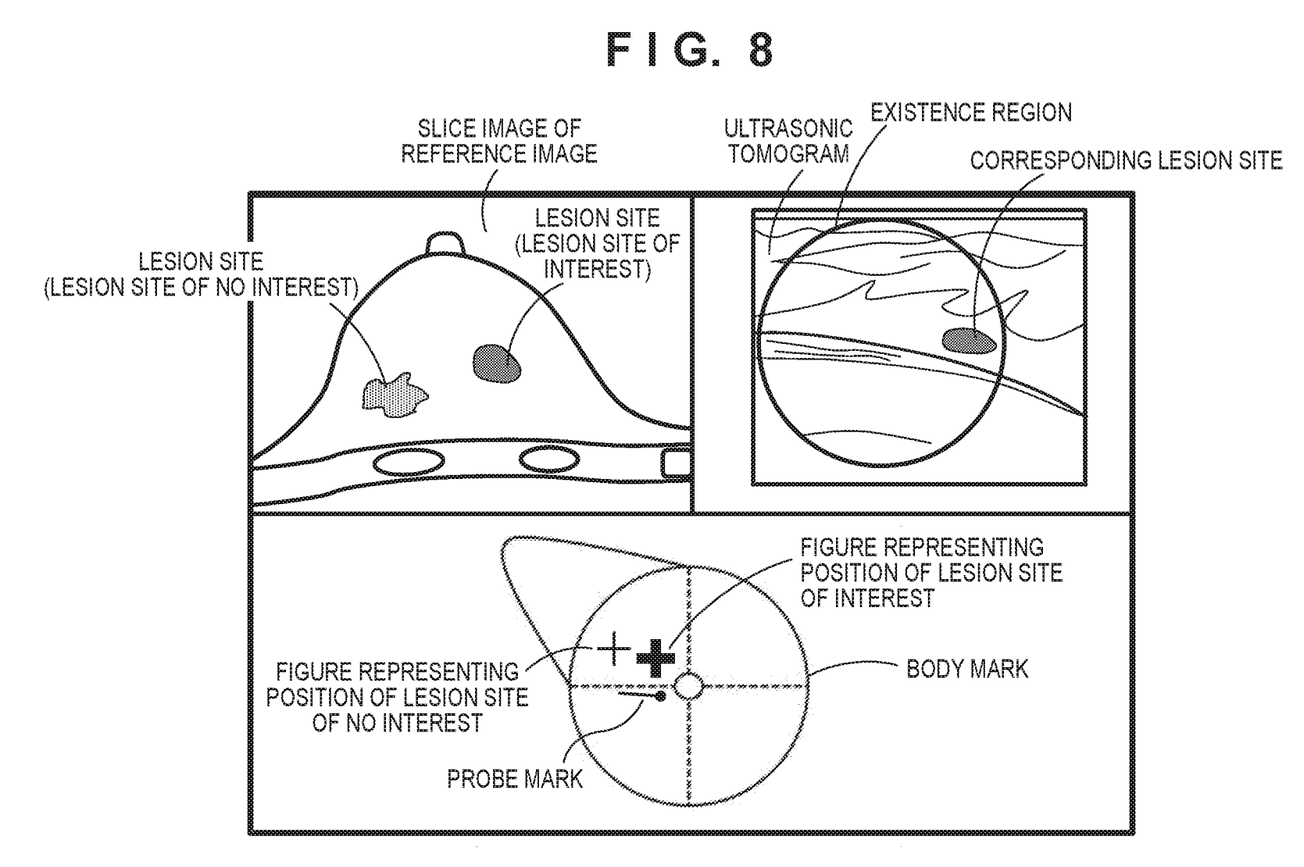
FIG. 8 is a view for explaining a display method by the image processing apparatus according to the second embodiment.

In step S7095, the image composition unit 640 generates a slice image, an image in which the existence region of the lesion site of interest is superimposed on the ultrasonic tomogram, and an image in which the lesion position is rendered on the body mark image. Then, for example, the image composition unit 640 aligns these images, generating a composite image as shown in FIG. 8. FIG. 8 shows a composite image made up of three images. The top left image is a slice image of a reference image containing a two-dimensional slice of a 3-D volume of a breast and cross-sections of ribs. The slice corresponds in the 3-D image data to the position of an ultrasonic tomogram. On the left is a lesion site of no interest that is shaded in a shade lighter than the right-hand lesion site of interest. The top right image shows the corresponding ultrasonic tomogram containing the corresponding lesion site as a shaded shape and an existence region shown as a circle. Finally, the bottom image shows a body mark with a left-hand cross representing a position of the lesion site of no interest and a right-hand, darker cross as a figure representing a position of the lesion site of interest. There is also illustrated a mark representing the ultrasonic probe position.

As processing of the display control unit 150, the image composition unit 640 displays the composite image on the display unit 160. In accordance with change of the region of interest, the display control unit 150 deletes, from the ultrasonic image, the display of an existence region corresponding to a region of interest serving as the region of interest before the change. The deletion includes displaying an image in which no existence region is superimposed on an ultrasonic image in accordance with change of the region of interest.

From another viewpoint, the display control unit 150 controls the display unit 160 to display the positions of respective regions of interest on a body mark (first image), and display an existence region representing the existence range of a selected region of interest on an ultrasonic image (second image) in accordance with a selection by the region-of-interest selection unit 122. In this case, in accordance with change of the region of interest, the display control unit 150 switches the display from the existence region of a region of interest before the change to the existence region of a region of interest after the change. The display control unit 150 controls a display so as not to display, on the ultrasonic image (second image), the existence region of an unselected region of interest among a plurality of obtained regions of interest. Also, in accordance with a selection, the display control unit 150 displays the position of the selected region of interest by using the first figure on the body mark (first image), and display the position of the unselected region of interest by using the second figure different from the first figure. The display control unit 150 displays the position of the ultrasonic probe on the body mark (first image).

If necessary, the composite image is output outside via an I/F 1009, and stored in the RAM 1002 so that it can be used from another application.

Processing in step S7100 is the same as that in step S3100 in the first embodiment, and a description thereof will not be repeated.

As described above, the image processing apparatus according to the second embodiment can change the display mode of a figure representing the position of a lesion site of no interest on a body mark so that the figure becomes less conspicuous than a figure representing the position of a lesion site of interest. In addition, the image processing apparatus can change, to non-display, the display mode of a figure representing the existence region of a lesion site of no interest on an ultrasonic tomogram. By observing the body mark, the operator can grasp whether a lesion site which may cause an identification error exists near the lesion site of interest.

Since a figure representing the existence region of a lesion site of no interest is not displayed on the ultrasonic tomogram, it does not hinder search for a corresponding lesion site. That is, the image processing apparatus according to the second embodiment can efficiently search a target image for a corresponding lesion site corresponding to a lesion site of interest selected from a plurality of lesion sites in a reference image, and identify the lesion site of interest.

In the above-described embodiment, a slice image obtained by extracting a slice identical to an ultrasonic tomogram from three-dimensional image data serving as a reference image, and the ultrasonic tomogram are presented side by side. However, the slice image need not always be displayed. In this case, neither obtainment of three-dimensional image data serving as a reference image nor slice image generation processing may be executed.

(Modification 1 to Second Embodiment)

The above-described embodiment has exemplified a case in which the color of a figure representing the position of a lesion site of no interest in a body mark representing a target object is changed into a light color. However, the display mode change method is not limited to this. For example, the thickness or type of the line of the figure may be changed, or the saturation of the color of the figure may be decreased.

When, for example, the position of a lesion site of no interest is spaced apart from a lesion site of interest by a predetermined distance, and the lesion site of interest is less likely to be erroneously identified as a lesion site of no interest, the display control unit 150 does not display a figure representing the position of the lesion site of no interest in the body mark representing the target object. That is, the display control unit 150 restricts display of the position of a region of interest on the first image based on the positional relationship between the existence region of a selected region of interest and the position of an unselected region of interest. This can make the display more recognizable.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An information processing apparatus comprising at least one processor and memory coupled to each other and cooperating to act as:
    an obtaining unit configured to obtain a target position included in a first image of an object imaged by a first apparatus, wherein the first image is a three-dimensional medical image;
    an estimating unit configured to estimate, in a three-dimensional coordinate system, a position of a second image imaged by a second apparatus different from the first apparatus that corresponds to the target position, wherein the second image is a tomographic image;
    a determining unit configured to determine whether or not the second image and a three-dimensional existence region cross each other in the three-dimensional coordinate system, wherein the three-dimensional existence region is obtained by adding a predetermined circumference range to the position corresponding to the target position, wherein the three-dimensional existence region is a region where the corresponding position corresponding to the target position may exist; and
    a display control unit configured to display on a display unit information indicating the three-dimensional existence region over the second image when it is determined that the second image and the three-dimensional existence region cross each other, and to display on the display unit information indicating a three-dimensional position of the target position when it is determined that the second image and the three-dimensional existence region do not cross each other.

2. The information processing apparatus according to claim 1, wherein the display control unit displays, on the display unit, the information indicating the three-dimensional position of the target position and the second image in a case in which it is determined that the second image and the three-dimensional existence region do not cross each other.

3. The information processing apparatus according to claim 1, wherein the display control unit does not display, on the display unit, the information indicating the three-dimensional position of the target position in a case in which it is determined that the second image and the three-dimensional existence region cross each other.

4. The information processing apparatus according to claim 1, wherein the display control unit displays, on the display unit, the information indicating a distance and a direction based on the three-dimensional position in a case in which it is determined that the second image and the three-dimensional existence region do not cross each other.

5. The information processing apparatus according to claim 2, wherein the display control unit displays, on the display unit, the information indicating a distance and a direction based on the three-dimensional position in a case in which it is determined that the second image and the three-dimensional existence region do not cross each other.

6. The information processing apparatus according to claim 3, wherein the display control unit displays, on the display unit, the information indicating a distance and a direction based on the three-dimensional position in a case in which it is determined that the second image and the three-dimensional existence region do not cross each other.

7. The information processing apparatus according to claim 1, wherein the three-dimensional existence region is defined as a sphere having a center of the corresponding position corresponding to the target position.

8. The information processing apparatus according to claim 7, where an existence region in the second image is displayed as a region where the second image crosses the sphere.

9. The information processing apparatus according to claim 7, where the region where the second image crosses the sphere is displayed as a circle.

10. The information processing apparatus according to claim 1, wherein the information indicating the three-dimensional position comprises information indicating three dimensional directions to the target position.

11. The information processing apparatus according to claim 1, wherein the information indicating the three-dimensional position is represented by a figure.

12. The information processing apparatus according to claim 1, wherein the second image is successively imaged by the second apparatus.

13. The information processing apparatus according to claim 1 wherein the first apparatus is a magnetic resonance imaging (MRI) apparatus or an X-ray computed tomography (CT) apparatus.

14. The information processing apparatus according to claim 1, wherein the target position comprises a position of a lesion.

15. The information processing apparatus according to claim 1, wherein the information indicating the three-dimensional existence region comprises information indicating a region in which the target position may exist in the second image.

16. An information processing method comprising:
obtaining a target position included in a first image of an object imaged by a first apparatus;
estimating, in a three-dimensional coordinate system, a position of a second image imaged by a second apparatus different from the first apparatus that corresponds to the target position, wherein the second image is a tomographic image;
determining whether or not a second image and a three-dimensional existence region cross each other in the three-dimensional coordinate system, wherein the three-dimensional existence region is obtained by adding a predetermined circumference range to the position corresponding to the target position, wherein the three-dimensional existence region is a region where the corresponding position corresponding to the target position may exist; and
displaying on a display unit information indicating the three-dimensional existence region over the second image when it is determined that the second image and the three-dimensional existence region cross each other, and displaying on the display unit information indicating a three-dimensional position of the target position when it is determined that the second image and the three-dimensional existence region do not cross each other.

17. An non-transitory computer-readable storage medium storing a program which causes a computer to execute an information processing method, the method comprising:
obtaining a target position included in a first image of an object imaged by a first apparatus;
estimating, in a three-dimensional coordinate system, a position of a second image imaged by a second apparatus different from the first apparatus that corresponds to the target position, wherein the second image is a tomographic image;
determining whether or not a second image and a three-dimensional existence region cross each other in a three-dimensional coordinate system, wherein the three-dimensional existence region is obtained by adding a predetermined circumference range to the position corresponding to the target position, wherein the three-dimensional existence region is a region where the corresponding position corresponding to the target position may exist; and
displaying on a display unit information indicating the three-dimensional existence region over the second image when it is determined that the second image and the three-dimensional existence region cross each other, and displaying on the display unit information indicating a three-dimensional position of the target position when it is determined that the second image and the three-dimensional existence region do not cross each other.

* * * * *